United States Patent [19]

Stieg

[11] Patent Number: 5,304,287
[45] Date of Patent: Apr. 19, 1994

[54] MICRODISTILLATION METHOD

[75] Inventor: Scott Stieg, Milwaukee, Wis.

[73] Assignee: Lachat Instruments, Milwaukee, Wis.

[21] Appl. No.: 652,186

[22] Filed: Feb. 7, 1991

Related U.S. Application Data

[62] Division of Ser. No. 408,681, Sep. 18, 1989, Pat. No. 5,022,967.

[51] Int. Cl.$^5$ ............................................. B01D 3/00
[52] U.S. Cl. ................................ 203/1; 159/DIG. 27; 159/DIG. 28; 203/12; 203/99; 203/DIG. 2; 436/158; 436/178
[58] Field of Search .................. 203/95, 92, 12, 99, 203/DIG. 2, 1; 159/DIG. 27, DIG. 28; 436/178, 158

[56] References Cited

U.S. PATENT DOCUMENTS

| | | | |
|---|---|---|---|
| 1,917,272 | 7/1933 | Podbielniak | 203/DIG. 2 |
| 2,608,528 | 8/1952 | Piros et al. | 203/DIG. 2 |
| 3,303,634 | 2/1967 | Berrian | 159/DIG. 27 |
| 3,305,595 | 2/1967 | Paulson | 585/819 |
| 3,340,157 | 9/1967 | Weiss | 203/DIG. 2 |
| 3,455,792 | 7/1969 | Ohta | 203/40 |
| 3,765,981 | 10/1973 | Rodgers | 159/DIG. 27 |
| 3,776,970 | 12/1973 | Strazik et al. | 585/819 |
| 3,878,054 | 4/1975 | Rodgers | 203/1 |
| 3,985,624 | 10/1976 | Prevost et al. | 203/1 |
| 4,089,749 | 5/1978 | Karamian | 203/DIG. 2 |
| 4,092,117 | 5/1978 | Byrne | 436/178 |
| 4,267,150 | 5/1981 | Firestone | 203/DIG. 2 |
| 4,476,024 | 10/1984 | Cheng | 210/500 |
| 4,545,862 | 10/1985 | Gore et al. | 159/DIG. 27 |
| 4,604,263 | 8/1986 | Smernoff | 436/178 |
| 4,620,900 | 11/1986 | Kimura et al. | 202/172 |
| 4,746,437 | 5/1988 | Koseki et al. | 159/DIG. 27 |
| 4,789,526 | 12/1988 | Matkovich | 422/101 |
| 4,806,313 | 2/1989 | Ebersole et al. | 422/101 |
| 4,895,808 | 1/1990 | Remer | 436/178 |
| 4,959,197 | 9/1990 | Parekh et al. | 422/101 |
| 4,971,915 | 11/1990 | Schwartz et al. | 436/139 |
| 4,973,485 | 11/1990 | Rich | 426/651 |
| 5,000,919 | 3/1991 | Heckmann | 436/178 |
| 5,015,332 | 5/1991 | Iwaga et al. | 159/DIG. 28 |

FOREIGN PATENT DOCUMENTS

| | | | |
|---|---|---|---|
| 0608534 | 5/1978 | U.S.S.R. | 202/238 |
| 1566253 | 4/1980 | United Kingdom | 422/101 |

Primary Examiner—Virginia Manoharan
Attorney, Agent, or Firm—Foley & Lardner

[57] ABSTRACT

A microdistillation method for the quantitative steam distillation of cyanide, phenolic compounds, hydrogen fluoride, ammonia, sulfites and other volatile analyte compounds from samples of environmental waters and sludge for their subsequent analysis involves volatilizing the water in the sample tube of a microdistillation column. The pressure which develops due to the water vapor forces all volatile compounds from the water sample, including the water itself, through a hydrophobic membrane and into the collector tube of the microdistillation column. The volatile compounds and the water vapor condense in the cooler collector tube and are quantitatively trapped and retained over the membrane. Relatively small samples may be distilled.

15 Claims, 7 Drawing Sheets

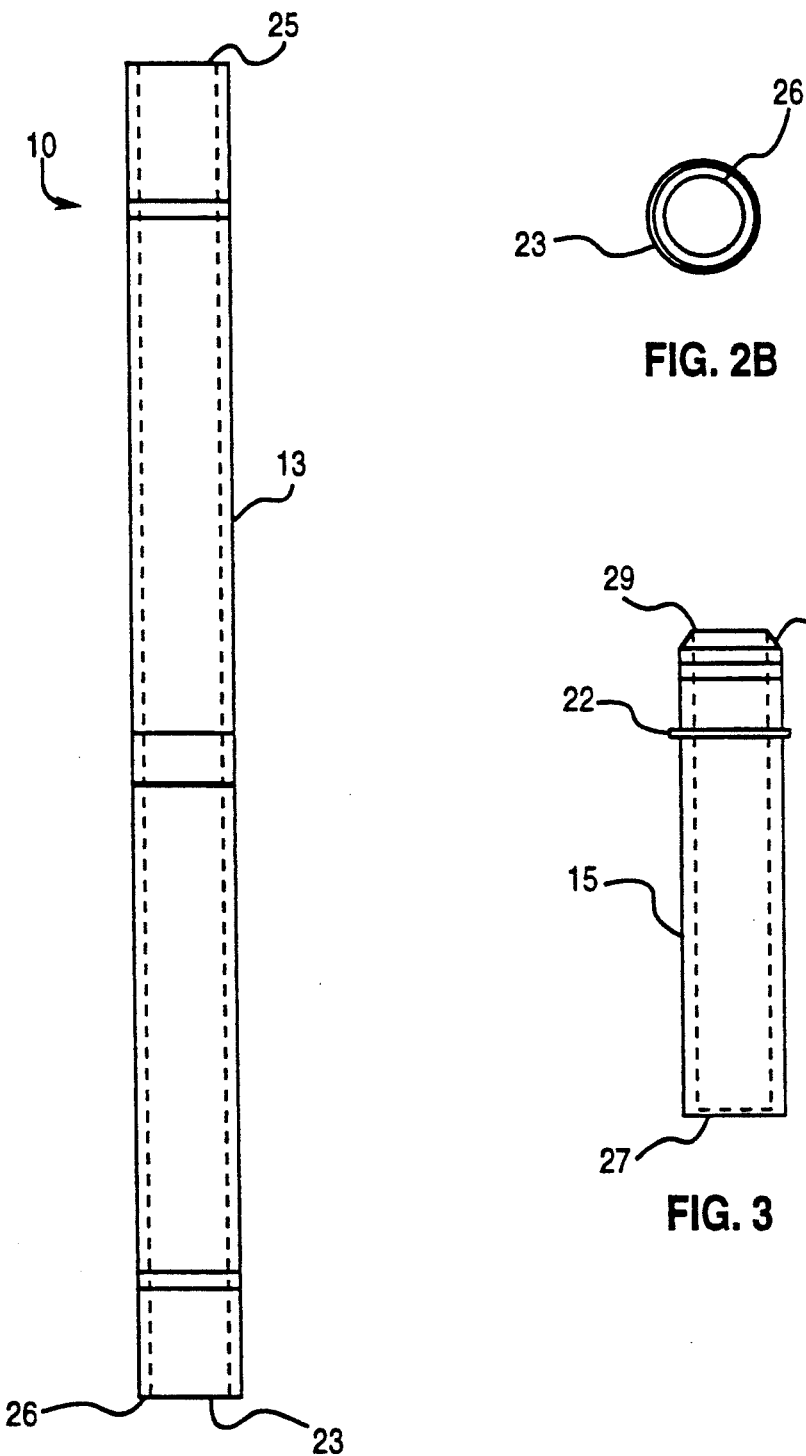

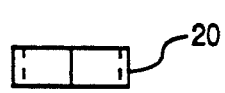
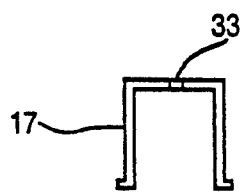
FIG. 4A
FIG. 5A
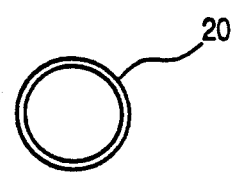
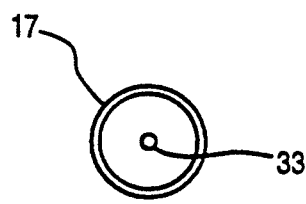
FIG. 4B
FIG. 5B

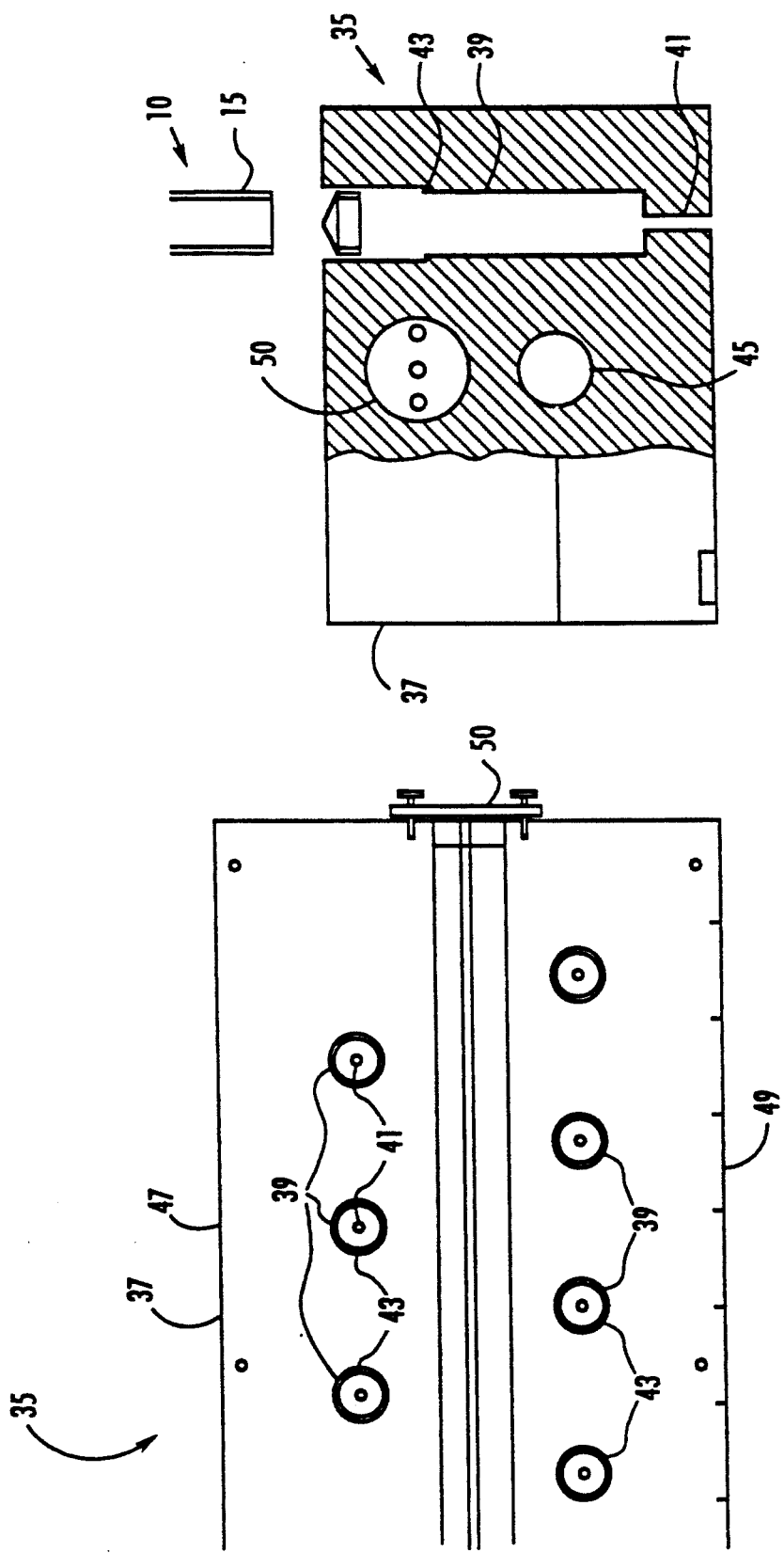

MICRODISTILLATION METHOD

This is a divisional of U.S. Ser. No. 07/408,681 filed on Sep. 18, 1989, now U.S. Pat. No. 5,022,967.

BACKGROUND OF THE INVENTION

The present invention relates to a microdistillation apparatus and process for the removal of volatile analyte compounds from samples obtained from waste water and other sources.

United States Environmental Protection Agency (EPA) standardized methods for the determination of several chemical species in environmental samples have been established for several years. Based on the technique of flow injection analysis, these methods provide rapid, accurate and precise determinations.

However, for some analytes, notably cyanide, phenolic compounds, ammonia, hydrogen fluoride, volatile acids, sulfides and sulfites, samples must first be taken through a complicated and time consuming distillation process to remove the analyte from a potentially interfering matrix prior to automated analysis. As a result, the analyst has been required to use a low-throughput, large volume manual distillation apparatus and method involving classical vaporization, condensation and collection with expensive and fragile macro-scale glassware.

FIGS. 8 and 9 are examples of the aforementioned current state of the art with respect to macrodistillation apparatus. With these and other systems distillation usually requires two to three hours for completion. These macrodistillation apparatus also typically require as much as 500 milliliters (mL) of sample and therefore can distill only up to five samples simultaneously on an eight foot laboratory bench. Irregular contact between the sample and the mantle is another problem which results in variable heating. When in use these apparatus generate considerable waste heat which often necessitates the use of a fume hood. In addition, current macrodistillation systems employ a water-cooled condenser so that flood safety mechanisms must also be provided for. Transfer is necessary after distillation since the distillate does not end up in a sampler-ready tube. Furthermore, with the current systems there are many separate pieces to both assemble and clean.

Some continuous-flow analyzers employ a flowing-stream digestion and distillation device in which the sample to be determined is fed continuously first into a flow-through UV-irradiation digestion device, and then into a microdistillation chamber. This achieves at best 20 sample/h throughput, with full baseline resolution. These devices also require 30 to 60 minutes of start-up flow to stabilize.

It is now known in the art to utilize hydrophobic membranes to assist in the separation of distillate from distillant. Such membranes are disclosed, for example, in Ohta, U.S. Pat. No. 3,455,792; Cheng, U.S. Pat. No. 4,476,024; Kimura et al., U.S. Pat. No. 4,620,900; and Rodgers, U.S. Pat. No. 3,878,054. However, these membranes are presently employed in conjunction with relatively cumbersome and/or complex distillation apparatus and methods designed to permit a relatively large volume of product to be distilled.

The prior art is thus replete with distillation devices especially well-suited for generating a large volume of distillate, often continuously, for relatively large-scale industrial syntheses. None of these devices are directed towards distillation on a smaller analytical scale, however.

Thus, there presently exists a need for a microdistillation system and method which is relatively simple and which does not require a large volume of sample for efficacy, and therefore is appropriate for analytical-scale distillations of less than 500 mL.

SUMMARY OF THE INVENTION

The present invention advantageously provides a microdistillation apparatus and method which facilitates the simple, fast and accurate purging or steam distillation of volatile analyte compounds from samples of environmental water, sludges, soils, and other sources. The microdistillation column itself is easy to assemble and use. Furthermore, the microdistillation apparatus and process according to the present invention advantageously permits the utilization of relatively small quantities of samples for distillation.

The microdistillation column comprises a collector tube having a top end and an open bottom end. A sample tube with an open top end is fitted to the open bottom end of the collector tube. Within the sample tube is provided means for holding a volumetric sample of a liquid to be distilled.

At least one hydrophobic, porous membrane is interposed above the top end of the sample tube for trapping and retaining substantially all condensate of at least a portion of a liquid sample which is to be volatilized in the sample tube and passed through the membrane into the collector tube during a distillation procedure. Additionally, means for removably sealing the top end of the collector tube is also provided.

A method for the microdistillation of liquid samples containing volatile analyte compounds comprises the steps of:

1) placing a volumetric sample of a liquid in a sample tube with an open top end;

2) fitting the open top end of the sample tube to an open bottom end of a collector tube, the bottom end of the collector tube being fitted with at least one hydrophobic, porous membrane; and 3) volatilizing at least a portion of the volumetric sample such that the volatilized sample passes through the membrane, condenses in the collector tube, and is then retained over the membrane.

A heating block apparatus especially well-adapted for use with the aforementioned microdistillation column and method is also provided. The heating block can be utilized for the simultaneous distillation of a plurality of liquid samples, and comprises a base, a heating element contained within the base which is a substantially cylindrical cartridge heater, and means for holding the liquid samples to be distilled.

BRIEF DESCRIPTION OF THE DRAWINGS

FIG. 2A is a side elevation view of a collector tube comprising part of the microdistillation column illustrated in FIG. 1.

FIG. 2B is a top view of the sample tube comprising part of the microdistillation column illustrated in FIG. 1.

FIG. 3 is a side elevation view of a sample tube comprising part of the microdistillation column illustrated in FIG. 1.

FIG. 4A is a side elevation view of a mounting ring used in conjunction with the microdistillation column illustrated in FIG. 1.

FIG. 4B is a bottom plan view of the mounting ring illustrated in FIG. 4A.

FIG. 5A is a side elevation view of a cap used in conjunction with the microdistillation column illustrated in FIG. 1.

FIG. 5B is a bottom plan view of the cap illustrated in FIG. 5A.

FIG. 6A is a top plan view of a heating block included as part of the invention and used for volatilizing liquid samples contained in the microdistillation column of FIG. 1.

FIG. 6B is an exposed side view, with parts broken away, showing the heating block illustrated in FIG. 6A.

DETAILED DESCRIPTION OF THE PREFERRED EMBODIMENTS

Figure 1:
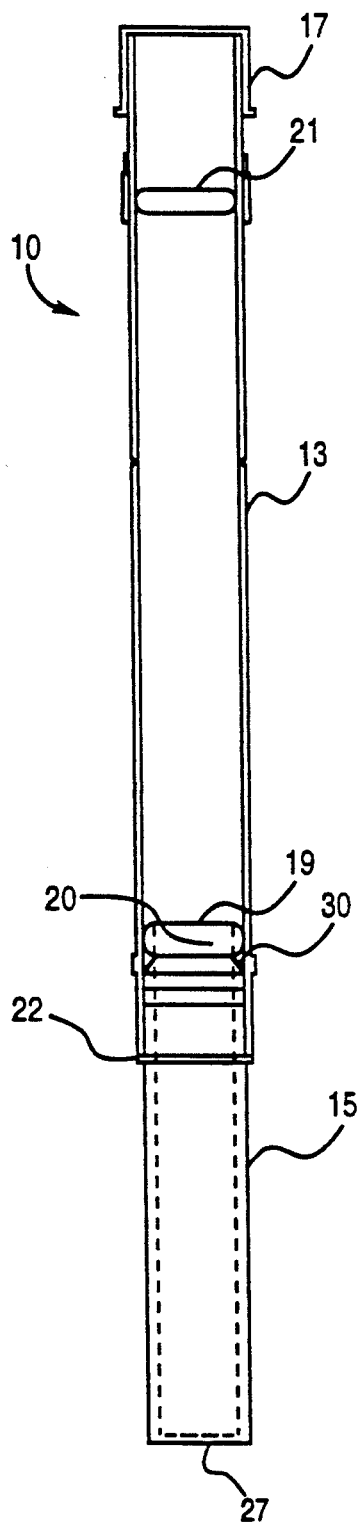
FIG. 1 is a side elevation view of a microdistillation column according to the present invention.

Referring now to the drawings where like numerals represent like parts, FIG. 1 shows a microdistillation column 10 which is utilized for the distillation of liquid samples containing volatile analytes, e.g. cyanides, phenols, sulfites, sulfides, volatile acids, ammonia, hydrogen fluoride and other compounds. The microdistillation column 10 is preferably substantially cylindrical in shape from top to bottom. The column further comprises a collector tube 13, a sample tube 15 fitted to the bottom of the collector tube, and preferably a cap 17 fitted over the top of the collector tube. At least one hydrophobic, porous membrane 19 is positioned above the sample tube 15. Between the membrane 19 and the sample tube 15 may be a membrane mounting ring 20. At least one other hydrophobic capping membrane 21 is preferably fitted between the collector tube 13 and the cap 17. The sample tube may also have an optional mounting step 22 around its outer circumference which abuts the bottom of the collector tube 13. Each of the aforementioned microdistillation column components is hereinafter described.

Referring also to FIGS. 2A and 2B, the collector tube 13 is comprised of a material with a passive thermal gradient so that the top portion of the collector tube remains relatively cool when the sample tube of the microdistillation column 10 is subjected to the temperatures necessary to volatilize the liquid contained therein. Preferably, a clear polymer material is used for the collector tube. Polypropylene is especially preferred as a polymer material since it exhibits desirable thermal and chemical properties.

The collector tube 13 has an open bottom end 23 and an open top end 25. As shown in FIG. 2B, it is desirable that the bottom end 23 have a chamfered segment 26 so that the sample tube 15 can be fitted to this chamfered segment. A seal between the collector tube 13 and the sample tube 15 can therefore be more easily attained. The top end 25 of the collector tube is fitted with the hydrophobic capping membrane or the cap, and preferably both.

Referring also to FIG. 3, the sample tube 15 has a closed bottom end 27 and an open top end 29. The sample tube further comprises means for holding a volumetric sample with liquid to be distilled. The open top end 29 of the sample tube 15 is fitted to the open bottom end 23 of the collector tube 13. The open top end 29 can have a chamfered segment 30 which is inversely chamfered relative to the chamfered segment 26 of the open bottom end 23 of the collector tube 13 so that a leak-proof seal therebetween can be formed.

In assembling the microdistillation column 10 in preparation for the distillation of a liquid sample, one or more of the hydrophobic, porous membranes 19 are first fitted to the open bottom end 23 of the collector tube 13. It is preferred to use only one or two membrane(s) 19 for this purpose for reasons of economics. It is especially desirable to fit the membrane 19 to the inside circumference of the bottom end 23 of the collector tube 13. Although those skilled in the art may conceive of numerous ways of doing this, the goal is to achieve a leak-proof seal which will preclude the reverse transmission of any liquid which has been volatilized in the sample tube and has passed through the membrane and condensed in the collector tube.

Referring also to FIGS. 4A and 4B, a membrane mounting ring 20 can be utilized to fit the membrane 19 to the inside circumference of the bottom end 23 of the collector tube 13. If the bottom end 23 contains the chamfered segment 26, then the mounting ring 20 and the membrane 19 are pushed up inside the bottom end past this chamfered segment 26 and come to rest at a position above the chamfered segment. The design of the chamfered segment facilitates the placing of the membrane without tearing. Those skilled in the art may find it useful to invert the collector tube 13 in order to position the membrane and the mounting ring inside the bottom end of the collector tube. In the event the membrane is torn or stretched during positioning, then it should be replaced with a fresh one.

As previously mentioned, the membrane 19 is preferably hydrophobic and porous. This means that it will permit volatilized compounds and water to pass through and yet will preclude any reverse transmission of the condensate. Polymer membranes made of polytetrafluoroethylene marketed under the trade names Teflon ® and Zitex ®, are especially well known in the art. Other polymer membranes may be used so long as they are hydrophobic and porous and possess the requisite integrity demanded by the chemical and thermal environment, including resiliency to elevated temperatures and to acids and bases. Preferably, any membrane used should have a pore size in the range of from about 0.2 to about 0.5 micrometers; more preferably, about 0.4 micrometers. It is also desirable that the thickness of an individual membrane be in the range of from about five thousandths of an inch (0.005) to about fifteen thousandths of an inch (0.015).

Once the membrane 19 has been fitted to the collector tube 13, the collector tube is then positioned so that the top open end 25 is up. A small quantity of a trapping solution may optionally be added to the collector tube above the membrane if the sample to be distilled contains, e.g., cyanide, ammonia, or other volatile acid or base. The trapping solution under such circumstances is preferably dilute NaOH or dilute $H_2SO_4$, and the quantity added is proportional to the quantity of sample to be distilled. Thus, for a 7 mL sample there would be added about 1 to about 2 mL of trapping solution. The trapping solution can be added to the collector tube 13 by any method known in the art, for example by pipet, and will come to rest above the membrane. If the sample to be volatilized contains phenol or other analytes, then water may be added as a trapping solution in proportional quantities as specified above.

After the optional trapping solution has been added, it is desirable to position the capping membrane 21 over the top open end 25 of the collector tube so as to form a seal. The capping membrane is also preferably hydrophobic and is most preferably a polymer membrane such as polytetrafluoroethylene.

Referring also to FIGS. 5A and 5B, the cap 17 is provided which may be used in conjunction with the capping membrane 21 for sealing the top open end 25 of the collector tube 13. The cap 17 is also comprised of a polymer material and is designed to fit securely over the top end of the collector tube after the capping membrane has been positioned therein.

Preferably, the cap 17 contains a pin hole 33 through its top surface. As the cap is fitted over the top end 25 of the collector tube 13 pressure tends to build up inside the collector tube. The distillation process itself can also create pressure inside the collector tube as the result of hot air expansion. This build-up of pressure can blow out the membrane 19 positioned near the bottom end 23. The pin hole 33 acts to equalize pressure and thereby minimize this tendency. With the cap 17 in place, a volumetric sample to be distilled is added to the sample tube 15. This can be done by directly pipeting the liquid sample into the sample tube, or by any other known means. Those skilled in the art may find it desirable to add the sample to a suitable container which can be adapted to fit inside the sample tube. While the sample tube has been designed to hold relatively small quantities of liquid, it is certainly within the scope of the invention to vary the overall size of the sample tube in conjunction with the other components of the microdistillation column to accomodate larger or smaller quantities of liquid sample.

The sample tube 15 illustrated in FIG. 3 can preferably hold from about 0.1 to about 10 mL of sample, with the desired quantity for distillation being in the range of from about 4 to about 8 mL, most preferably 7 mL. If the sample contains dilute cyanide, then a quantity of dilute $H_2SO_4$, $MgCl_2$ releasing solution may be added in an amount proportional to the sample to be distilled. Thus, to a 7 mL sample would be added about 1 mL of about 6M $H_2SO_4$, 1M $MgCl_2$ releasing solution.

Once the sample and any optional acidifying or otherwise releasing solution has been added to the sample tube 15 then the sample tube is press-fitted by the user and sealed to the bottom end 23 of the collector tube 13. The chamfered segment 26 of the collector tube 13 and the inverse chamfered segment 30 of the sample tube 15 will facilitate joining the two tubes. The collector tube is pushed over the sample tube until the membrane mounting ring 20 almost abuts the top end 29 of the sample tube 15. Care should be exercised during this process to prevent dislodging the mounting ring and the membrane 19.

The sample tube 15 may also optionally contain a mounting stop 22 positioned around its outer circumference. When the sample tube is fitted to the collector tube 13, the stop 22 will press against the bottom end 23 of the collector tube 13. The stop further facilitates sealing the collector and sample tubes, and also prevents the sample tube from being pushed too far up into the collector tube.

Referring also to FIGS. 6A and 6B, there is provided as part of the invention a heating block 35 especially well-adapted for distilling the liquid sample contained in the assembled microdistillation column 10. The heating block 35 comprises a base 37 which can be made of a material already known in the art, e.g. aluminum, which is designed to ensure constant and even heating of the liquid samples.

Since those skilled in the art may wish to distill many liquid samples at one time, the base of the heating block can be fitted with a relatively large number of cavities 39 for receiving a like number of microdistillation columns containing samples. While there is conceivably no limit to the size of the heating block 35 and number of cavities 39 contained in the base therein, preferably the block will contain about 5 to about 30 cavities, preferably about 15 to about 25. Each cavity can optionally be provided with a bottom vent 41 to assist in clean-up.

It is desirable to additionally fit each cavity with at least one internal step 43. The step 43 serves two functions. The first is to provide a stop against which the underside of the mounting stop 22 will lie once the assembled microdistillation column 10 is positioned in the cavity. The second is to permit the temperature of the air below the stepped portion 43 to be raised, further ensuring even heating of the sample contained in the microdistillation column.

As illustrated in FIG. 6A, the cavities 39 are preferably positioned so as to be equidistant from an internal cartridge heater 45 which will extend approximately the length of the heating block 35. The cartridge heater 45, comprised of a known heating alloy, is preferably substantially cylindrical in shape and is contained within the base 37 so as to be substantially parallel with the section of the cavities 39 that is below the stepped portion 43. At the same time, it is desirable to fit the cartridge heater at roughly an equal distance from sides 47 and 49 of the heating block. In this way, cavities can be positioned on either side of the cartridge heater. The heating block 35 is further equipped with a thermocouple and thermostat 50 for setting the temperature at which the samples will be distilled. For microdistillation of samples containing water and volatile analytes the thermostat is set at a temperature in the range of about 100# to about 150# C., preferably about 125# to about 145# C. Variations are certainly possible depending upon the accuracy of the particular thermostat utilized.

Once the heating block 35 has been pre-heated to a suitable temperature for distillation, the assembled microdistillation column 10 with sample intact is then positioned in a cavity 39. Preferably, this is done so that the underside of the mounting stop 22 rests on the step 43 contained within each cavity. The membrane 19 and at least the upper portion of the mounting ring 20 will preferably be a small distance above the heating block itself. In one embodiment, the mounting ring and membrane will be about 1 to about 2 mm above the block. In this way, the distillate which will collect above the membrane 19 is prevented from re-volatilizing, and at the same time, sample immediately below the level of the membrane is prevented from refluxing.

The microdistillation column 10 will fit snugly, but not tightly, in the cavity 39. Furthermore, the positioning of the microdistillation column 10 in the heating block should be such that the collector tube of each column, when positioned therein, will present an outer face to the air for even cooling, eliminating the need for an elaborate and expensive liquid cooling mechanism currently utilized with many macrodistillation apparatus. Also eliminated is the need for a fume hood; distillation may be carried out on an open laboratory bench.

With the microdistillation column(s) positioned in the cavities 39 in the pre-heated block 35, distillation will commence and can easily be observed. The sample will boil and the pressure which then develops due to the water vapor will force all volatile compounds from the water sample, including the water vapor itself, through the hydrophobic, porous membrane 19 and into the collector tube 13. Condensation will then occur such that the distillate will gather in the collector tube and will lie over the membrane 19. The hydrophobic nature of the membrane 19 prevents the distillate from seeping back into the sample tube 15. Thus, substantially all distillate will be retained over the membrane.

While distillation may be terminated at any time once a sufficient quantity of distillate to permit the further analysis thereof can be visually observed in the collector tube 13, it is preferred to permit all the liquid sample to distill and condense in the collector tube. (Any soil particles or other non-volatile solid material suspended in the liquid will remain in the sample tube throughout the distillation process). For samples containing cyanide, complete distillation will usually take about 25 to about 35 minutes. About 50 to about 70 minutes will normally be necessary for complete distillation of those samples containing phenols. The time for set-up, complete distillation, and transfer of distillate will vary slightly depending upon a number of factors, but should be considerably less than the two to three hours currently required with standard macrodistillation apparatus.

Once the desired quantity of distillate has been trapped in the collector tube 13 above the membrane 19, the microdistillation column 10 is then removed from the cavity 39 in the heating block 35. The sample tube 15 is then separated from the collector tube 13. Any hot solution remaining in the sample tube is carefully disposed of; the sample tube itself can then be quickly rinsed for future use, or can also be disposed of.

The collector tube 13 containing the distillate can then be inverted to rinse the sides to allow the solution therein to homogenize. After rinsing, the collector tube and distillate are then allowed to cool for a few minutes, e.g., by placing the collector tube in a beaker or in a rack. Care should be exercised so that the entire bottom end 23 of the collector tube is not pressed against the resting surface.

Once cooled, the cap 17 is then removed from the collector tube 13 and saved. The capping membrane 21 over the top open end 25 of the collector tube is preferably discarded, as these should only be used for one distillation. The distillate is then poured into a suitable container for further analysis. Using Lachat Instrument's cyanide method, e.g. QuikChem method 10-204-00-1-A, there should be enough sample from the collector tube for three determinations. It is best to complete this analysis on the same day as the distillation, if possible. The membrane 19 at the bottom end 23 of the collector tube 13 is also preferably discarded. The collector tube and mounting ring 20 can be rinsed for future use, or may also be discarded.

Figure 7:
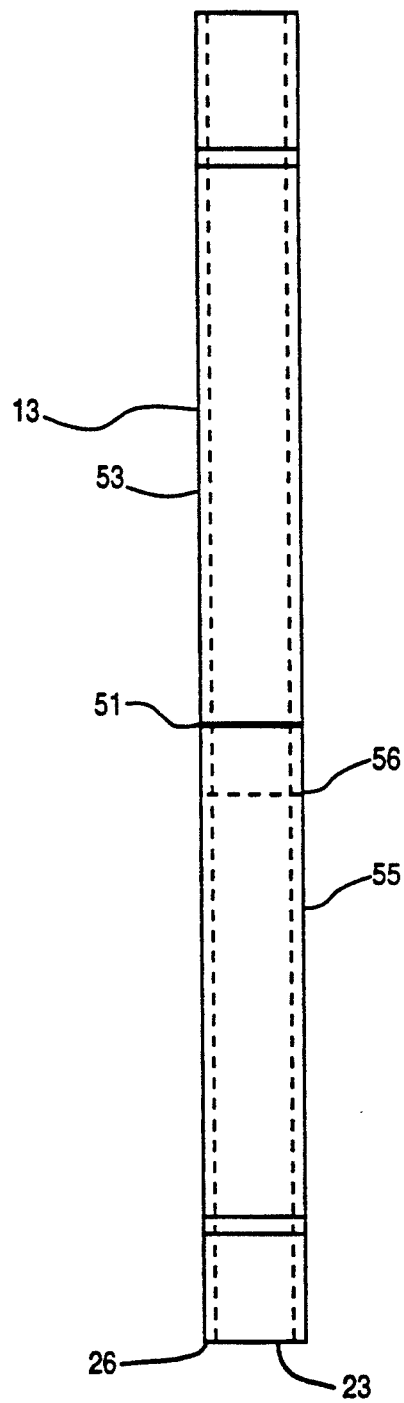
FIG. 7 is a side elevation view of a second embodiment of a collector tube.
Figure 8:
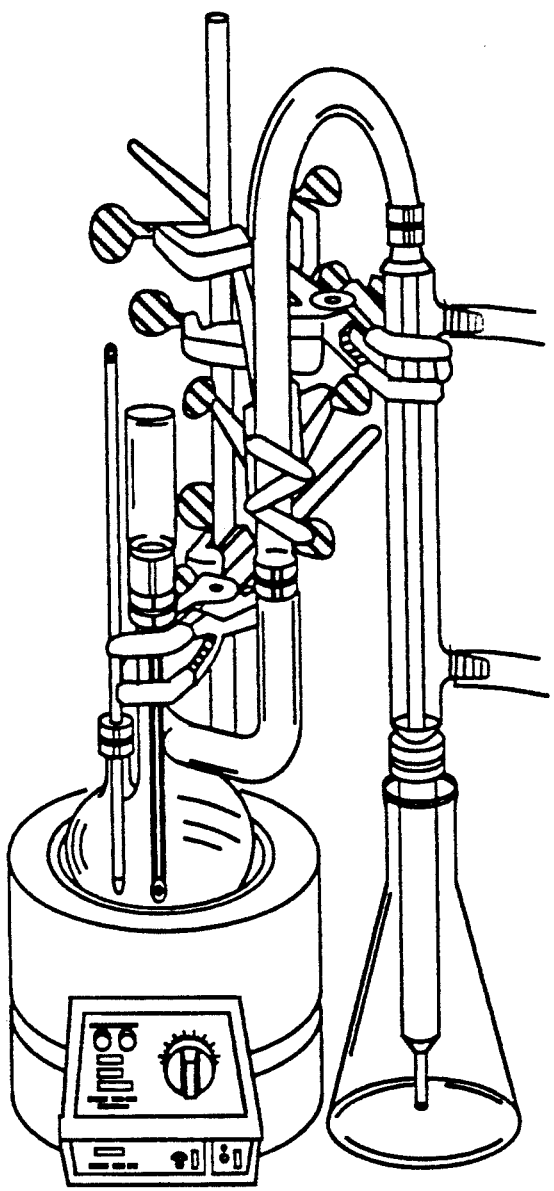
FIGS. 8 and 9 are examples of the current state-of-the-art with respect to macrodistillation apparatus.
Figure 9:
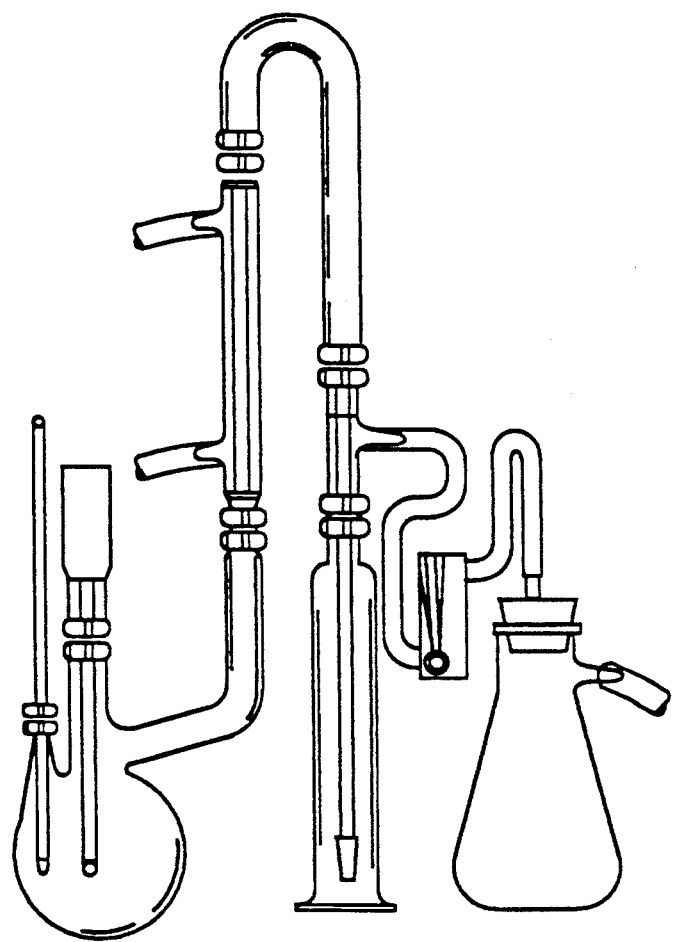

FIG. 7 illustrates another embodiment of the collector tube 13. This embodiment is nearly identical to the one illustrated in FIGS. 2A and 2B, except for the addition of a break-away mark 51 positioned on the outside circumference of the collector tube 13. The procedure for assembling the microdistillation column and distilling a liquid sample is nearly identical to that described previously, except that, after distillation, the collector tube 13 can then be severed at the break-away mark 51. The top section 53 of the severed collector tube above the mark is then discarded, and the bottom section 55 below the mark containing the distillate is then fitted with the cap 17. Prior to fitting the cap, the distillate in the bottom section can be made up to the volumetric mark 56 with water. In this way, the bottom section 55 can serve as a further analysis vessel. Analysis with QuikChem method 10-204-00-1-A is the same as described above.

EXAMPLES

The following tests were conducted to better illustrate the apparatus and method according to the invention, and should in no way be construed as limiting the scope of the invention.

Average measured sample responses are listed for several concentrations (mg/L) of analyte. Average measured sample responses are given in units of peak area absorbance for the particular concentration of analyte, and were calculated by adding Responses 1, 2, and 3 and then dividing by three. Responses 1, 2, and 3 were measured with an EPA-approved method which uses the Lachat Instruments QuikChem analyzer using colorimetry. Mean recovery was then calculated by dividing the average measured sample responses for sets of three concentrations of distilled samples by the average measured sample responses for sets of three concentrations of undistilled samples, and then multiplying by one hundred percent (100%). (In all Examples, the distilled samples represent the distillate obtained using the microdistillation column and method according to the invention. All samples were completely distilled until little or no liquid remained in the sample tube. The quantity of sample placed into the sample tube 15 in each Example was 7 mL.)

Example 1
Distilled Sample of Cyanide

| Conc. | Response 1 | Response 2 | Response 3 | Av. Rsp. |
|---|---|---|---|---|
| 0.5 | 1289 | 1298 | 1303 | 1297 |
| 0.2 | 479 | 480 | 480 | 480 |
| 0.1 | 227 | 228 | 229 | 228 |
| Undistilled Sample of Cyanide | | | | |
| 0.5 | 1219 | 1225 | 1219 | 1221 |
| 0.2 | 509 | 513 | 515 | 512 |
| 0.1 | 255 | 258 | 259 | 257 |

Mean Recovery: 96.1%

Example 2
Distilled Sample of Cyanide

| Conc. | Response 1 | Response 2 | Response 3 | Av. Rsp. |
|---|---|---|---|---|
| 0.1 | 305 | 306 | 306 | 306 |
| 0.05 | 153 | 153 | 153 | 153 |
| 0.02 | 59 | 61 | 59 | 60 |
| Undistilled Sample of Cyanide | | | | |
| 0.1 | 286 | 286 | 289 | 287 |
| 0.05 | 135 | 133 | 133 | 134 |
| 0.02 | 47 | 47 | 47 | 47 |

Mean Recovery: 109%

Example 3
Distilled Sample of Cyanide

| Conc. | Response 1 | Response 2 | Response 3 | Av. Rsp. |
|---|---|---|---|---|
| 0.02 | 52 | 51 | 52 | 52 |
| 0.01 | 17 | 18 | 16 | 17 |
| 0.005 | 10 | 11 | 12 | 11 |
| Undistilled Sample of Cyanide | | | | |
| 0.02 | 45 | 47 | 46 | 461 |
| 0.01 | 18 | 18 | 18 | 18 |

-continued

| 0.005 | 6 | 5 | 5 | 5 |

Mean Recovery: 110% (for 0.02 and 0.01 conc.s only,
0.005 approaches the detection limit of the QuikChem analyzer)
Average Mean Recovery For Examples 1, 2, and 3:
105% (EPA guidelines specify a range of 90–110%)

Example 4
Distilled Sample of Phenol

| Conc. | Response 1 | Response 2 | Response 3 | Av. Rsp. |
|---|---|---|---|---|
| 0.5 | 1244 | 1268 | 1257 | 1256 |
| 0.2 | 562 | 557 | 560 | 559 |
| 0.1 | 308 | 306 | 307 | 307 |

Undistilled Sample of Phenol

| 0.5 | 1316 | 1331 | 1326 | 1324 |
| 0.2 | 519 | 532 | 533 | 528 |
| 0.1 | 268 | 266 | 267 | 267 |

Mean Recovery: 105% (EPA guidelines specify a range of 90–110%)

The foregoing description has been set forth merely to illustrate the invention and is not intended to be limiting. Since modifications of the described embodiments incorporating the spirit and substance of the invention may occur to persons skilled in the art, the scope of the invention should be limited solely with respect to the appended claims and equivalents.

What is claimed is:

1. A method for the microdistillation of liquids containing volatile analyte compounds, which comprises the steps of:
    placing a volumetric sample of a liquid in a sample tube, said sample tube having an open top end;
    fitting said open top end of said sample tube to an open bottom end of a collector tube, said bottom end of said collector tube being fitted with at least one hydrophobic, porous membrane;
    positioning a capping member proximate the top end of said collector tube;
    volatilizing at least a portion of said volumetric sample such that said volatilized sample passes through said membrane; condensing said volatilized sample in said collector tube; retaining the condensate over said membrane; and chemically analyzing said condensate.

2. The method as claimed in claim 1, wherein said volumetric sample is not greater than about 10 mL.

3. The method as claimed in claim 2, wherein said volumetric sample is not greater than about 5 mL.

4. The method as claimed in claim 3, wherein said volumetric sample is not greater than about 0.1 mL.

5. The method as claimed in claim 1, further comprising the step of removing said condensate from said collector tube.

6. The method as claimed in claim 5, wherein said condensate is homogenized in said collector tube prior to said removal therefrom.

7. The method as claimed in claim 1, wherein said collector tube contains a trapping solution above said hydrophobic membrane.

8. The method as claimed in claim 1, wherein a mounting ring is utilized to position said membrane inside said bottom end of said collector tube prior to fitting said sample tube to said collector tube.

9. A microdistillation method for purging and trapping volatile analyte compounds from a volumetric sample containing the volatile analyte compounds, said method comprising the steps of:
    placing the volumetric sample in a microdistillation column including a collector tube having a top end and an open bottom end, a sample tube having means for holding the volumetric sample and an open top end, said open top end of said sample tube being fitted to said open bottom end of said collector tube, and at least one hydrophobic, porous membrane interposed above said top end of said sample tube in close proximity to said bottom end of said collector tube in spaced relation from the volumetric sample;
    volatilizing at least a portion of said volumetric sample such that said portion passes through said membrane and condenses in said collector tube, said membrane retaining substantially all condensate of said portion of the volumetric sample volatilized;
    placing a trapping medium in said collector tube above said hydrophobic membrane, wherein when said volatilizing step is carried out, said membrane permits said end portion of volumetric sample to pass through thereby conveying the purged analyte to said trapping medium, said membrane further preventing reverse transmission of said trapping medium and said condensate; and chemically analyzing said condensate.

10. The method of claim 9, further comprising the step of removing said condensate and said trapping solution from said collector tube.

11. The method as claimed in claim 10, wherein said step of removing comprises:
    severing the top section of said collector tube at a break-away mark;
    increasing the amount of fluid in the bottom section of said collector tube to a predetermined level; and,
    capping said bottom section with a polymer material.

12. The method as claimed in claim 9, further comprising the steps of positioning a capping membrane over the top open end of said collector tube so as to form a seal, and capping said collector tube top end with a polymer material.

13. The method as claimed in claim 9, wherein said step of placing the volumetric sample in said microdistillation column comprises placing a volumetric sample of not greater than about 10 mL in said sample tube.

14. The method as claimed in claim 13, wherein said step of placing the volumetric sample in said microdistillation column comprises placing a volumetric sample of not greater than about 5 mL in said sample tube.

15. The method as claimed in claim 9, further comprising the steps of removing said condensate from said collector tube and disposing of said microdistillation column.

* * * * *